United States Patent [19]

Glass et al.

[11] Patent Number: 4,845,194

[45] Date of Patent: Jul. 4, 1989

[54] GLYCOPEPTIDE RECOVERY PROCESS

[75] Inventors: Suzanne L. E. Glass; Charles W. Johnson; John L. Spencer, all of Indianapolis, Ind.

[73] Assignee: Eli Lilly and Company, Indianapolis, Ind.

[21] Appl. No.: 19,914

[22] Filed: Feb. 27, 1987

[51] Int. Cl.⁴ ............................................. C07K 3/12
[52] U.S. Cl. .................................. 530/344; 530/322; 530/317; 435/71
[58] Field of Search ....................... 530/317, 322, 344; 435/70, 71

[56] References Cited

U.S. PATENT DOCUMENTS

| | | | |
|---|---|---|---|
| 2,786,831 | 3/1957 | Bartels et al. | 260/210 |
| 2,990,329 | 6/1961 | Philip et al. | 167/65 |
| 3,067,099 | 12/1962 | McCormick et al. | 167/65 |
| 3,660,279 | 5/1972 | Hoff | 210/19 |
| 4,122,168 | 10/1978 | Michel | 424/118 |
| 4,239,751 | 12/1980 | Coronelli et al. | 424/118 |
| 4,322,406 | 3/1982 | Debono et al. | 424/118 |
| 4,440,753 | 4/1984 | McCormick et al. | 424/124 |
| 4,461,723 | 7/1984 | Hershberger et al. | 530/322 |
| 4,462,942 | 7/1984 | Hamill et al. | 260/112.5 R |
| 4,537,770 | 8/1985 | Michel et al. | 424/118 |
| 4,547,488 | 10/1985 | Merkel | 514/10 |
| 4,548,924 | 10/1985 | Michel | 514/10 |
| 4,548,925 | 10/1985 | Higgins et al. | 514/10 |
| 4,552,701 | 11/1985 | Nagarajan et al. | 530/322 |
| 4,558,036 | 12/1985 | Merkel | 530/322 |
| 4,639,433 | 1/1987 | Hunt et al. | 530/322 |
| 4,643,987 | 2/1987 | Nagarajan et al. | 530/322 |
| 4,645,827 | 2/1987 | Malabarba et al. | 530/322 |

FOREIGN PATENT DOCUMENTS 0241758 10/1987 European Pat. Off. .

OTHER PUBLICATIONS

P. A. Belter et al., "Development of a Recovery Process for Novobiocin", *Biotechnology and Bioengineering* 15, 533–549 (1973).

S. C. O'Connor, "Macroreticular Resin Chromatography of Antibiotics", *Methods Enzymol,* 43, 296–299 (1975).

*Primary Examiner*—Delbert R. Phillips
*Assistant Examiner*—T. D. Wessendorf
*Attorney, Agent, or Firm*—Nancy J. Harrison; Leroy Whitaker

[57] ABSTRACT

An improvement in the large-scale recovery of vancomycin-type glycopeptide antibiotics which comprises (1) commingling the fermentation medium in which the antibiotic is produced with a polystyrene divinylbenzene resin such as Dow XFS-43278.00, (2) separating the resin from the medium and (3) eluting the antibiotic from the resin. This improvement avoids preliminary filtration and pH adjustment of the broth, simplifies waste-disposal problems and eliminates antibiotic losses due to mycelial adsorption and filtration.

22 Claims, No Drawings

GLYCOPEPTIDE RECOVERY PROCESS

SUMMARY OF THE INVENTION

This invention provides an improvement in the large-scale recovery of vancomycin-type glycopeptide antibiotics. The improvement comprises: (1) adsorbing the antibiotic from the fermentation medium in which it is produced onto a polystyrene divinylbenzene resin such as Dow XFS-43278.00, (2) separating the resin from the fermentation broth and (3) eluting the antibiotic from the resin. The advantages of this improved process are (1) it permits direct use of the fermentation broth without prior pH adjustment, filtration or other purification procedure, thereby avoiding unnecessary losses of the antibiotic, and (2) it eliminates certain waste-disposal problems associated with prior processes such as the problem of disposing of filter aids.

DETAILED DESCRIPTION OF THE INVENTION

Vancomycin-type glycopeptide antibiotics are a valuable group of antibiotics. Vancomycin is a commercially successful antibiotic which has been available since the late 1950's. Illustrative members of the group of glycopeptide antibiotics which includes vancomycin are listed in Table I.

TABLE I

| Vancomycin-type Glycopeptide Antibiotics | |
|---|---|
| Antibiotic | Reference |
| vancomycin | U.S. Pat. No. 3,067,099, issued December 4, 1962 |
| M43A | U.S. Pat. No. 4,548,925, issued October 22, 1985 |
| M43D | U.S. Pat. No. 4,547,488, issued October 15, 1985 |
| M43B and M43C | U.S. Pat. No. 4,548,924, issued October 22, 1985 |
| A82846A, A82846B and A82846C | U.S. application serial No. 909,791, filed September 19, 1986 |
| ristocetin | U.S. Pat. No. 2,990,329, issued June 27, 1961 |
| ristocetin A pseudo-aglycone | Williams et al., J.C.S. Chem. Comm. 1979, 906–908 |
| A41030 factors A–G | U.S. Pat. No. 4,537,770, issued August 27, 1985 |
| A47934 | U.S. Pat. No. 4,462,942, issued July 31, 1984 |
| A35512 factors A–D and H | U.S. Pat. No. 4,122,168, issued October 24, 1978 |
| A35512B pseudo-aglycone[a] | U.S. Pat. No. 4,029,769, issued June 14, 1977 |
| actaplanin (A-4696) factors A and B | U.S. Pat. No. 4,115,552, issued September 19, 1978 |
| actaplanin factors $B_1$, $B_2$, $B_3$, $C_{1a}$, $C_{2a}$, D, $D_2$, $C_3$ and $E_1$ | U.S. Pat. No. 4,322,406, issued March 30, 1982 |
| actaplanin factor G | U.S. Pat. No. 4,461,723, issued July 24, 1984 |
| actaplanin factor H | U.S. Pat. No. 4,558,036, issued December 10, 1985 |
| actaplanin factors K–O | U.S. Pat. No. 4,479,897, issued October 30, 1984 |
| actaplanin pseudo-aglycone | U.S. Pat. No. 4,322,343, issued March 30, 1982 |
| teichomycin (teichoplanin) $A_1$, $A_2$ and $A_3$ | U.S. Pat. No. 4,239,751, issued December 16, 1980 |
| teichomycin $A_2$ factors 1–5 | U.S. Pat. No. 4,542,018, issued September 17, 1985 |
| L 17054 | U.S. Pat. No. 4,594,187, issued June 10, 1986 |
| L 17046 | European Patent 119,574-A |

[a]Called A35512B aglycone in the patent, but called A35512B pseudoaglycone herein since it retains the amino sugar.

For convenience in discussions herein, this group of compounds will be called vancomycin-type antibiotics.

Vancomycin-type antibiotics are useful as therapeutic agents, particularly against Gram-positive bacteria, and also as animal growth promoters.

An object, when recovering a vancomycin-type antibiotic from the fermentation broth in which it is produced, is to recover a maximum amount of the antibiotic using a minimum number of steps. Maximum recovery is even more difficult when the antibiotic is produced on a large scale. In such cases, the antibiotic must be isolated from large amounts of a complex aqueous fermentation mixture. The whole fermentation broth in which the antibiotic is produced contains not only the antibiotic, but also contains insoluble mycelia suspended in a dilute solution of unreacted medium nutrients and miscellaneous metabolic intermediates and products. Isolation of the antibiotic, therefore, is usually difficult and requires a number of separation, concentration and purification steps.

In most cases, the first step in recovering an antibiotic which has been produced by fermentation is adding a filter aid such as Hyflo Supercel. The principal benefit of the filter aid is to separate the mycelia more efficiently. When fermentation is carried out on a large scale, however, large amounts of the filter aid are required. Since filter aids are not readily biodegradable, their use in large-scale processes presents a substantial problem in waste disposal.

After removing the mycelia, a second step frequently used in recovering an antibiotic produced by fermentation is adjusting the pH of the filtered broth to an appropriate level. The large amounts of acid or base required for such a step, however, pose problems in safety and handling and increase the volume of solution to be handled.

Previously, in the commercial preparation of vancomycin, the whole broth was filtered at an alkaline pH of about 8 to 10, the pH of the filtrate was adjusted to about 6 to 7, and the filtrate was then passed across an ion-exchange resin, typically a low cross-linked polystyrene-divinylbenzene sodium cation-exchange resin. Vancomycin was adsorbed on the resin. Once the broth was removed, the resin was washed with water and vancomycin was eluted with an aqueous alkaline solution of pH 9–11. A typical solvent for elution was aqueous sodium hydroxide of pH 10–11. The alkaline eluate containing the vancomycin was neutralized, and the activity was further purified by readsorbing the vancomycin onto a non-functional resin (see U.S. Pat. No. 4,440,753).

The improved process of this invention permits direct use of the fermentation broth without pH adjustment and/or filtration. Thus, losses of the antibiotic due to adsorption on the mycelia and associated mechanical losses are eliminated. Furthermore, certain waste-disposal problems, such as those associated with the filter aid and any pH adjustment, are avoided.

The process of this invention also uses a polystyrene divinylbenzene resin, such as Dow XSF-43278.00, to adsorb the vancomycin-type glycopeptide antibiotic from the fermentation broth, but does not require prior filtration, pH adjustment or other purification procedures. The process steps comprise: (1) commingling the fermentation broth in which the vancomycin-type glycopeptide antibiotic is produced (the whole broth) with a polystyrene divinylbenzene resin, (2) separating the resin from the remaining fermentation broth, and (3) eluting the antibiotic from the resin.

A significant aspect of the process of this invention is a special type of ion-exchange resin. This resin, which is a sulfonated copolymer of styrene and divinylbenzene, is called a polystyrene divinylbenzene resin herein for convenience. The resin is a microporous, strong-acid-cation resin with low crosslinkage (nominally 2%) which is usually in a salt form such as the sodium salt. Examples of suitable resins for this process are Dow XFS-43278.00 (Dow Chemical Co., Midland, MI, U.S.A.) and Diaion SK-102 (Mitsubishi Chemical Industries, Ltd., Tokyo, Japan). We have discovered that this type of resin may be used to adsorb vancomycin-type glycopeptide antibiotics without the previously required step of first filtering the whole fermentation broth.

The amount of resin used in the process will vary with the volume of the fermentation medium and the amount of antibiotic activity produced by the fermentation. Generally, the resin is commingled with the whole fermentation broth, either by adding the whole broth to the resin or by adding the resin to the whole broth, for sufficient time to permit the antibiotic to be adsorbed onto the resin.

The length of contact time required for the antibiotic to adsorb to the resin will vary. For example, the temperature of the broth affects the length of time which is required. In a preferred procedure, warming the broth to a temperature of from about 30° to about 60° decreases the contact time needed and also makes the broth less viscous and, therefore, easier to handle. The time required will generally be up to about six hours.

Following the adsorption of the antibiotic on the resin, the fermentation medium can be separated from the resin using known techniques, e.g. filtration (when the resin is added by batch contact) or mechanical separation (when mixing the resin and the broth by upflow adsorption).

The antibiotic can then be eluted from the separated resin, using procedures in the art. An especially advantageous procedure comprises (1) washing the resin with water, (2) eluting the antibiotic by slurrying the resin batch-wise in water adjusted to a pH of from about 9 to about 12 until the antibiotic is released from the resin and (3) separating the eluate containing the antibiotic from the resin. A pH of from about 10 to about 11 is especially preferred for step (2) of this procedure.

The antibiotic can be recovered from the eluate and optionally further purified by a variety of known procedures. For example, the soluble antibiotic can be further purified by adsorbing it onto a nonfunctional resin, as discussed supra. Another method is to isolate the antibiotic as an insoluble copper complex. The copper complex can then be treated with hydrogen sulfide under acidic conditions to solubilize the antibiotic, which can be isolated as a free base by suitable pH adjustment.

The free base can be used in formulations for oral administration or it can be converted to an appropriate acid-addition salt such as a hydrochloride or phosphate for use in formulations for oral or parenteral administration.

Although the process of this invention is advantageous for any member of the group of vancomycin-type antibiotics, the antibiotics for which it is most suitable are those produced by fermentation processes, i.e. vancomycin, M43A, B, C and D, A82846A, B and C, ristocetin, A41030 factors A-G, A47934, A35512 factors A-D and H, actaplanin factors A, $B_1$, $B_2$, $B_3$, $C_{1a}$, $C_3$, $E_1$, G and H, and teichomycins $A_1$, $A_2$ factors 1-5 and $A_3$. The process is particularly suitable for vancomycin which, because of its commercial success, is frequently produced on a very large scale.

The following examples illustrate the operation of this invention.

PREPARATION 1

Preparation of Antibiotic A82846

(a) Fermentation of the A82846-Producing Cultures (1) Using the NRRL 18098 Culture A. Shake-flask Fermentation of NRRL 18098

The culture *Nocardia orientalis* NRRL 18098, either as a lyophilized pellet or as a suspension maintained in liquid nitrogen, is used to inoculate a seed medium having the following composition:

| SEED MEDIUM | |
| --- | --- |
| Ingredient | Amount (%) |
| Glucose | 1.0 |
| Soluble starch | 2.0 |
| Yeast extract | 0.5 |
| Enzymatic hydrolysate of casein* | 0.5 |
| CaCO$_3$ | 0.1 |
| Deionized water | q.s. 1 liter |
| Adjust the pH of the medium to about 7.5 with NaOH before sterilizing. | |

*NZ Amine A, Sheffield Chemical Co., Norwich, NY

Slants or plates are prepared by adding 2.5% agar to the seed medium. The inoculated slant is incubated at 30° C. for from about 10 to about 14 days. The mature slant culture is scraped with a sterile tool to loosen the spores and remove and mascerate the mycelial mat. About one-fourth of the loosened spores and culture growth thus obtained is used to inoculate 50 mL of a first-stage seed medium. The inoculated first-stage medium is incubated in a 250-mL Erlenmeyer flask at 30° C. for about 24–hours on a shaker orbiting in a two-inch (5.08 cm) circle at 250 rpm This incubated first-stage medium (0.5 mL) is used to inoculate 50 mL of a production medium having the following composition:

| Ingredient | Amount (%) |
| --- | --- |
| Glucose | 2.5 |
| Soybean flour | 1.5 |
| Potato dextrin | 3.0 |
| CaCO$_3$ | 0.25 |
| Blackstrap molasses | 0.3 |
| Acid-hydrolyzed casein* | 0.5 |
| Deionized water | q.s. 1 liter |
| (Presterilization pH adjusted to 7.5 with NaOH) | |

*Hy-Case, Sheffield Chemical Co.

The inoculated production medium is incubated in a 250-mL wide-mouth Erlenmeyer flask at 30° C. for 4 to 5 days on a shaker orbiting in a two-inch circle at 250 rpm.

B. Tank Fermentation of NRRL 18098

In order to provide a larger volume of inoculum, 10 mL of incubated first-stage medium, prepared as described in Section A, is used to inoculate 400 mL of a second-stage growth medium having the same composition as that of the first-stage medium. This second-stage vegetative medium is incubated in a 2-L wide-mouth Erlenmeyer flask for about 48 hours at 30° C. on a shaker orbiting in a two-inch circle at 250 rpm.

Incubated second-stage vegetative medium (1000 mL) thus prepared is used to inoculate 100 liters of sterile production medium, prepared as described in Section A except that P-2000 antifoam (0.3 g/L) is added. The inoculated production medium is allowed to ferment in a 165-L stirred fermentation tank for 90 to 100 hours at a temperature of 30° C. The airflow in the stirred vessel (80 RPM) is adjusted to maintain a dissolved oxygen level above 50% of air saturation.

C. Alternate Tank Fermentation of NRRL 18098

The procedure of Section B is followed except that an appropriate amount of vegetative medium is used to inoculate approximately 1200 gallons of production medium in a 1600-gallon (4536-L) fermentation tank.

(2) Using the NRRL 18099 Culture

The culture *Nocardia orientalis* NRRL 18099, either as a lyophilized pellet or as a suspension maintained in liquid nitrogen, is cultured using the procedure described in Section (1) except that the production medium has the following composition:

| Ingredient | Amount (%) |
| --- | --- |
| Glucose | 1.0 |
| Potato dextrin | 2.0 |
| Peptone* | 1.0 |
| CaCO$_3$ | 0.2 |
| Blackstrap molasses | 2.0 |
| Deionized water | q.s. 1 liter |
| No pH adjustment | |

*Bacto-peptone (Difco Laboratories)

(3) Using the NRRL 18100 Culture

The culture *Nocardia orientalis* NRRL 18100, either as a lyophilized pellet or as a suspension maintained in liquid nitrogen, is cultured using the procedure described in Section (1) except that the acid-hydrolyzed casein used is Amicase (Sheffield Chemical Co.).

(b) Preparation of Crude A82846

Fermentation broth (4200 L) from a 1600-gallon fermenter, prepared as described in Section (a)(1)(A), was adjusted to pH 10.5 with 5N NaOH, and 3% Celite 545 (filter aid) was added. The mixture was filtered through a filter press, and the press was washed with water. The combined filtrate and wash (4200 L) was adjusted to pH 7 with 5N HCl (or H$_2$SO$_4$) and applied to a column of Dow XFS-43278 (NH$_4$+) resin (200 L filtrate/10 L resin). The column was eluted at a flow rate of 750 mL/min. Fractions were assayed either by bioassay using *Bacillus subtilis* or HPLC.

The column was washed with 5 column volumes of water, collecting 100-L aliquots.

The active material was eluted from the resin with 5 column volumes of 0.05N NH$_4$OH, collecting 25-L fractions. Fractions containing A82846 were combined and concentrated in vacuo to a volume of about 30 L. This solution was applied to a 10-L column of Diaion HP-20 resin in water. The column was washed with 3 column volumes of water at a flow rate of 300 mL/min. The water wash was discarded. The active material was eluted from the column with a solution of H$_2$O:iPrOH (95:5) containing 1.0% acetic acid at a rate of 100 mL/min, collecting 4-L fractions and assaying by bioassay and HPLC. Fractions containing A82846 (#6-14) were combined, concentrated in vacuo and freeze-dried to yield 356 g of crude A82846.

(c) A82846 HPLC Assay Method

The following analytical HPLC systems are useful for the A82846 components:

(1) Cation Exchange Resin Column

Column Support: Zorbax* SCX(4.6×150 mm).
System: Gradient Elution A:B (4:1) to A:B (1:9) in 5 min., hold for 15 min.
A=MeOH:0.1M NaH$_2$PO$_4$ (1:9).
B=MeOH:0.9M NaH$_2$PO$_4$ (1:9).
Flow Rate: 1.0 mL/min.
Detection: UV at 225 nm.
Retention Times: are concentration dependent, but are approximately:
A82846C=6.6 min
A82846B=8.9 min
A82846A=9.5 min (2) Reverse Phase Column Column Support: Zorbax* ODS (4.6×150 mm).
System: Gradient Elution 1% (NH$_4$)H$_2$PO$_4$:CH$_3$CN (95:5) to (1:1) in 20 min.
Flow Rate: 1.0 mL/min.
Detection: UV at 225 nm.
Retention Times:
A82846A=7.3 min
A82846C=7.6 min
A82846B=8.0 min

*Zorbax columns are products of E. I. duPont de Nemours & Co., Inc., Wilmington, Del. 19898.

(d) Isolation of the A82846 Components (1) Isolation of A82846A and A82846B

A. Separation of Enriched A82846A and A82846B

A82846 (30 g), prepared as described in Section (b), was dissolved in water (500 mL) and applied to a pressurized 30-L stainless-steel column of silica gel LP-1/C$_{18}$ equilibrated in 1% NH$_4$H$_2$PO$_4$. The column was developed using a gradient of 1% NH$_4$H$_2$PO$_4$ (60 L) to water:acetonitrile (88:12) containing 1% NH$_4$H$_2$PO$_4$ (60 L) at a flow rate of 250-300 mL/min (max pressure of 600 psi), collecting 4-L fractions and monitoring elution using a UV detector at 254 nm. Individual fractions were assayed by analytical HPLC. Fractions rich in A82846A (#6-9) and fractions rich in A82846B (#10-17) were each combined and concentrated in vacuo.

B. Purification of A82846A

A82846A-rich concentrates from two 30-g runs carried out as described in Sect. A were desalted on a 1750-mL column of Diaion HP-20 SS, washing with water, eluting with H$_2$O:iPrOH (95:5) containing 0.5% acetic acid and assaying by analytical HPLC. Fractions containing A82846A were combined, concentrated and freeze-dried to yield 7.4 g of A82846A-enriched preparation The A82846A-enriched preparation (7.2 g) was dissolved in water and applied to a preparative HPLC column of silica gel LP-1/C$_{18}$ in 1% (NH$_4$)H$_2$PO$_4$. The column was developed with a gradient of 1% (NH$_4$)H$_2$PO$_4$ to 1% (NH$_4$)H$_2$PO$_4$:acetonitrile (9:1), monitoring the elution by analytical HPLC at 254 nm and eluting at a flow rate of 48 mL/min. After the first 10 L was eluted, 500-mL fractions were collected.

Fractions containing A82846A (#4-10) and fractions containing A82846B (#12-20) were each combined and concentrated in vacuo. Concentrates of A82846A from 3 runs were combined and applied to a 1750-mL column of Diaion HP-20 SS to desalt the solution. The column was washed with water, and A82846A was eluted with $H_2O$:iPrOH (95:5) containing 0.5% acetic acid. Elution was monitored by HPLC. Fractions containing A82846A were combined, concentrated and freeze-dried to yield 7.9 g of purified A82846A.

C. Purification of A82846B

A82846B-enriched fractions from 3 preparative HPLC runs separating A82846A and A82846B, obtained as described in Section B, were combined and desalted on a 1750-mL column of Diaion HP-20 SS, washing with water and eluting with $H_2O$:iPrOH (95:5) containing 0.5% acetic acid. Elution was monitored by HPLC and the A82846B fractions were combined, concentrated in vacuo and freeze-dried to yield 8.8 g of purified A82846B.

D. Desalting

Desalting can also be accomplished using Diaion HP-20 resin and eluting with MeOH:$H_2O$ (4:1) containing 0.1% acetic acid.

(2) Isolation of A82846C

A. Separation of A82846

Fermentation broth (461 L), obtained from four 165-L fermentations carried out as described in Section (a)(1)(B), was adjusted to pH 10.5 with 5N NaOH and filtered with 3% Hyflo Supercel filter aid. The filtrate (430 L) was adjusted to pH 7 with 5N HCl and applied to a column containing 10 L of Dowex-XFS-43278 ($NH_4+$) resin. The column was washed with 50 L of water, and the active material was eluted with 0.05N $NH_4OH$ (50 L), collecting 4-L fractions. Elution was monitored by bioassay. Active fractions (#1-7) were combined, concentrated in vacuo to a volume of about 1700 mL and freeze-dried to yield 283.9 g of crude A82846.

B. Separation of A82846A, B and C

Crude A82846 (2 g), obtained as described in Section A, was dissolved in water and applied to a 2"× 45" stainless-steel preparative HPLC column containing 2110 mL of silica gel LP-1/$C_{18}$ resin in 1% $(NH_4)_2HPO_4$. The column was developed using a gradient of from 1% $(NH_4)_2HPO_4$ to 1% $(NH_4)_2HPO_4$:acetonitrile (92:8) at a flow rate of 70 mL/min. collecting 400-mL fractions and monitoring by UV at 254 mm.

Fractions containing A82846A (#11-14) were combined as pool 1; fractions containing A82846C (#16-20) were combined as pool 2; and fractions containing A82846B (#21-25) were combined as pool 3.

C. Purification of A82846C

Pool 2 was concentrated to a volume of about 200 mL and applied to a 7-×45-cm glass column containing 1800 mL of Diaion HP-20 resin for desalting. The active material was eluted with MeOH:$H_2O$ (4:1) containing 0.1% acetic acid, collecting 1-L fractions at a flow rate of 25 mL/min. Fractions containing C (#9-12) were pooled, concentrated in vacuo and freeze-dried to give 662.2 mg of semi-purified A82846C.

The semi-purified A82846C (500 mg) was further purified by repeating the reverse-phase HPLC steps, using a 1"×48" steel column containing 450 mL of silica gel LP-1/$C_{18}$, a gradient of 1% $(NH_4)_2HPO_4$ to 1% $(NH_4)_2HPO_4$:acetonitrile (92:8), a flow rate of 11 mL/min, collecting 25-mL fractions and monitoring at 254 nm. Fractions containing A82846C (#169-210) were pooled and desalted on a 5-×45-cm glass column containing HP-20 resin. The column was eluted with MeOH:$H_2O$ (4:1) containing 0.1% acetic acid, collecting 100-mL fractions and following the elution by analytical HPLC with UV at 225 nm. Fractions containing A82846C (#5-11) were combined, concentrated in vacuo and freeze-dried to yield 127.3 mg of A82846C.

Pool 1 containing A82846A and pool 3 containing A82846B were purified in the same manner described for A82846C to obtain additional purified A82846A and A82846B.

D. Further Purification of A82846C

A82846C (70 mg) was purified further using the following preparative chromatographic procedure:

Column: Zorbax SCX (9.2×250 mm) cation exchange.

Mobile Phase: A linear gradient starting from 0.15M $NaH_2PO_4$ buffer containing 10% MeOH to 0.9M $NaH_2PO_4$ buffer containing 10% MeOH in 6 min. and holding 5 min. (no adjustment made to the buffer).

Flow Rate: 6.0 mL/min.

Detection: UV at 280 nm.

Load: 6.0 mg/injection in $H_2O$.

A82846C was collected by use of an automated fraction collector (Gilson 201C) equipped with a peak detection mechanism. Mobile phase was delivered by a Millipore Waters M600 Gradient HPLC System, and sample solution was injected via a Hitachi autosampler.

Fractions containing A82846C were combined, concentrated to a volume of 30 mL and applied to an HP-20 column (50 mL). The column was washed with $H_2O$ and eluted with $H_2O$ isopropanol (95:5) containing 0.5% HOAc, collecting 25 mL fractions. Fractions containing A82846C (#9-14) were combined, concentrated and lyophilized to yield 37 mg of purified A82846C.

(e) Characteristics of the A82846 Components (1) A82846A

Molecular Weight: 1556.

Empirical Formula: $C_{73}H_{89}N_{10}O_{26}Cl$.

FAB-MS (thioglycerol): (M+1) Found: 1557.5803; Calcd. $C_{73}H_{90}N_{10}O_{26}Cl = 1557.5716$.

UV ($H_2O$) λmax: 281 nm ($\epsilon 5,052$), shifts to 300 nm with base.

IR (KBr): 1716, 1655, 1611, 1586, 1552, 1504, 1410, 1340, 1310, 1230, 1212, 1132, 1066, 1028 and 1015 $cm^{-1}$.

pKa ($H_2O$): 4.7, 9.5

(66% DMF): 5.5, 6.8, 7.9, 9.4, 12.3 (apparent mol. wt. 1542).

(2) A82846B

Molecular Weight: 1590.

Empirical Formula: $C_{73}H_{88}N_{10}O_{26}Cl_2$.

FAB-MS (thioglycerol): (M+1) Found: 1591.5315; Calcd. $C_{73}H_{89}N_{10}O_{26}Cl_2 = 1591.5327$.

UV ($H_2O$) λmax: 280 nm ($\epsilon 5,192$), shifts to 300 nm with base.

IR (KBr): 1656, 1586, 1562, 1504, 1403, 1264, 1230, 1135, 1105, 1065, 1023, and 1018 $cm^{-1}$.

pKa ($H_2O$): 4.65, 9.5.

(3) A82846C

Molecular Weight: 1522.

Empirical Formula: $C_{73}H_{90}N_{10}O_{26}$.

FAB-MS (thioglycerol): (M+Na) Found: 1545.5998; calcd. $C_{73}H_{90}N_{10}O_{26}Na = 1545.5925$.

UV (H$_2$O) λmax: 280 nm (ε5,198), shifts to 300 nm with base.

IR (KBr): 3600→3004 (broad), 2999, 2991, 2950, 1687→1650, (broad), 1585, 1570, 1509, 1503, 1453, 1449, 1402, 1212, 1130, 1102, 1060, 1032 and 1014 cm$^{-1}$.

pKa (H$_2$O): 4.6, 9.4.

(4) Other Characteristics

Amino acid analyses of A82846A, A82846B and A82846C, after hydrolysis with 6N HCl, indicated the presence of aspartic acid and two broad peaks with a trace of glycine. The two peaks appear to correspond to actinoidinic and vancomycinic amino acids, both of which are present in glycopeptides of the vancomycin class. Comparative NMR studies indicate that A82846A, A82846B and A82846C each contain the novel amino-sugar 4-epi-vancosamine (3-methyl-acosamine).

The molecular formula of A82846A corresponds to that of vancomycin (C$_{66}$H$_{75}$N$_9$O$_{24}$Cl$_2$) minus one chlorine atom plus the elements of an additional amino sugar of the vancosamine type (C$_7$H$_{14}$NO$_2$). The molecular formula of A82846B corresponds to that of A82846A in which a hydrogen atom is replaced by a chlorine atom. The molecular formula of A82846C corresponds to that of A82846A in which a chlorine atom has been replaced by hydrogen. Thus, the A82846 components appear to constitute a new family of glycopeptides which clearly resemble the vancomycin molecule in general composition, differing mainly in chlorine content and in the presence of an additional sub-unit having a vancosamine composition.

(f) Antibacterial Activity of the A82846 Antibiotics

The A82846 antibiotics have shown in vivo antimicrobial activity against experimentally-induced infections in laboratory animals. When two doses of test compound were administered to mice experimentally infected with the test organism, the activity observed was measured as an ED$_{50}$ value [effective dose in mg/kg to protect 50% of the test animals: see Warren Wick, et al., *J. Bacteriol.* 81, 233–235 (1961)]. ED$_{50}$ values observed for illustrative compounds are given in Table II.

TABLE II

| | In Vivo Activity of A82846 Antibiotics | | |
| --- | --- | --- | --- |
| | ED$_{50}$ Value[a] | | |
| Compound | *Staphylococcus aureus* | *Streptococcus pyogenes* | *Streptococcus pneumoniae* |
| A82846A | 0.19 | 0.19 | 0.17 |
| A82846B | 0.19 | 0.20 | 0.18 |
| A82846C | 2.18 | 2.71 | 5.87 |
| Vancomycin | 1.3 | 0.72 | 1.52 |

[a]mg/kg × 2; doses administered subcutaneously to mice 1 and 4 hours post-infection

EXAMPLE 1

Vancomycin Whole Broth Adsorption

Regenerated Dow XFS-43278.00 resin (1 L) was added to vancomycin whole broth containing 45.4 g of activity. After being stirred for six hours at room temperature, the broth was separated from the resin through a 100-mesh sieve. The spent broth was assayed for loss and discarded.

The loaded resin was washed with purified water and then eluted batchwise by adjusting the resin slurry to pH 10.5 with sodium hydroxide solution and stirring for two hours while maintaining the resin slurry at pH 10.5. The eluted resin was then separated from the eluate via vacuum filtration and washed with purified water. The collected eluate and washes were combined, adjusted to pH 3.1 with hydrochloric acid for solution stability, and assayed. The assays indicated that a recovery of 37.1 g of activity was accomplished.

The eluted resin is regenerated by slurrying for twenty minutes in an aqueous solution adjusted to pH 2.0 with hydroclonic acid, washing with purified water to remove excess acid, stirring for another twenty minutes with a sodium chloride solution to return the resin to its Na+ form, and then rinsing with purified water to remove any excess salt solution.

In contrast, using a similar amount of whole broth and the best prior art recovery scheme of pH adjustments and filtrations, only 23.2 g of vancomycin activity would be expected in the resin eluate.

EXAMPLE 2

M43A Whole Broth Adsorption

Antibiotic M43A is produced according to the procedure of U.S. Pat. NO. 4,548,925, Example 2, except that in Section B, the steps of (1) filtering the whole broth and (2) treating the filtrate with a cation exchange resin are eliminated. Instead, regenerated Dow XSF-43278.00 resin is added to the whole broth, the mixture is stirred for six hours at room temperature, and the broth is separated from the resin through a sieve. The loaded resin is treated as in Example 1 to recover the M43A. Purification of M43A is accomplished as described in U.S. Pat. No. 4,548,925, Example 2, Section C.

EXAMPLE 3

Actaplanin Whole Broth Adsorption

Actaplanin is produced as described in U.S. Pat. No. 4,322,406, Example 1, except that, in the isolation step in Section C, the steps of (1) adding the filter aid, (2) filtering the whole broth, (3) resuspending the filter cake in water, (4) adjusting the pH of the aqueous suspension to 10.5 and (5) filtering are eliminated. Instead, Diaion SK-102 is added to the whole broth, and the procedures of Example 1 are used to recover the actaplanin complex. Actaplanin factors B$_1$,B$_2$, B$_3$, C$_{1a}$, C$_3$ and E$_1$ are isolated as described in Sections D and F of Example 1 of the patent.

EXAMPLE 4

Teicoplanin Whole Broth Adsorption

Teicoplanin is produced as described in U.S. Pat. No. 4,239,751 (columns 4–6) except that the following steps are eliminated: filtering the broth, adjusting the pH of the filtered medium, extracting the medium with butanol, washing the mycelial cake with water at pH 3.5, drying it under vacuum, extracting it with aqueous acetone, concentrating the acetone extract, adjusting its pH and extracting it with butanol. Instead, the procedures of Example 1 are used to recover the teicoplanin complex.

EXAMPLE 5

A82846 Whole Broth Adsorption

Antibiotic A82846 is prepared as described in Preparation 1, sections (a)(3) and (b) except that the procedures of Example 1 are used in section (b) and the following steps are eliminated: adjusting the pH, adding the filter aid, filtering the mixture through a filter press, washing the press with water and adjusting the pH of the combined filtrate/wash.

We claim:

1. In a process for recovering a glycopeptide antibiotic selected from the group consisting of vancomycin, M43A, M43B, M43C, M43D, ristocetin, ristocetin A pseudoaglycone, A41030 factors A, B, C, D, E, F and G, A47934, A82846A, A82846B, A82846C, A35512 factors A, B, C, D and H, A35512B pseudoaglycone, actaplanin factors A, $B_1$, $B_2$, $B_3$, $C_{1a}$, $C_{2a}$, $C_3$, $D_1$, $D_2$, $E_1$, G, H, K, L, M, N and O, actaplanin pseudoaglycone, teichomycins $A_1$, $A_2$ and $A_3$, teichomycin $A_2$ factors 1, 2, 3, 4 and 5, L 17054 and L 17046 from the fermentation medium in which it is produced, and improvement which consists essentially of:

(1) adsorbing the antibiotic from the fermentation medium onto a sulfonated polystyrene divinylbenzene resin without (a) using a filter aid or (b) adjusting the pH;

(2) separating the resin from the medium; and (3) eluting the antibiotic from the resin with an aqueous solution having a pH of from 9 to 12.

2. A process of claim 1 in which the antibiotic is adsorbed from the fermentation medium by adding the medium to the resin by upflow adsorption.

3. A process of claim 1 in which the antibiotic is adsorbed by adding the resin to the medium by batch contact.

4. A process of claim 1 in which the antibiotic is vancomycin.

5. A process of claim 2 in which the antibiotic is vancomycin.

6. A process of claim 3 in which the antibiotic is vancomycin.

7. A process of claim 1 in which the antibiotic is M43A.

8. A process of claim 3 in which the antibiotic is M43A.

9. A process of claim 1 in which the antibiotic is M43D.

10. A process of claim 3 in which the antibiotic is M43D.

11. A process of claim 1 in which the antibiotic is ristocetin.

12. A process of claim 3 in which the antibiotic is ristocetin.

13. A process of claim 1 in which the antibiotic is selected from the group consisting of A41030 factors A, B, C, D, E, F and G.

14. A process of claim 3 in which the antibiotic is selected from the group consisting of A41030 factors A, B, C, D, E, F and G.

15. A process of claim 1 in which the antibiotic is selected from the group consisting of A82846A, A82846B and A82846C.

16. A process of claim 1 in which the antibiotic is selected from the group consisting of antibiotic A82846A, A82846B and A82846C.

17. A process of claim 1 in which the antibiotic is selected from the group consisting of A35512 factors A, B, C, D and H.

18. A process of claim 1 in which the antibiotic is selected from the group consisting of A35512 factors A, B, C, D and H.

19. A process of claim 1 in which the antibiotic is selected from the group consisting of actaplanin factors A, $B_1$, $B_2$, $B_3$, $C_{1a}$, $C_{2a}$, $C_3$, $D_1$, $D_2$, $E_1$, G and H 20. A process of claim 1 in which the antibiotic is selected from the group consisting of actaplanin factors A, $B_1$, $B_2$, $B_3$, $C_{1a}$, $C_{2a}$, $C_3$, $D_1$, $D_2$, $E_1$, G and H.

21. A process of claim 1 in which the antibiotic is selected from the group consisting of teichomycins $A_1$, $A_2$ and $A_3$ and teichomycin $A_2$ factors 1, 2, 3, 4 and 5.

22. A process of claim 3 in which the antibiotic is selected from the group consisting of teichomycins $A_1$, $A_2$ and $A_3$ and teichomycin $A_2$ factors 1, 2, 3, 4 and 5.

* * * * *

UNITED STATES PATENT AND TRADEMARK OFFICE
CERTIFICATE OF CORRECTION

PATENT NO. : 4,845,194

DATED : July 4, 1989

INVENTOR(S) : Suzanne L. E. Glass

It is certified that error appears in the above-identified patent and that said Letters Patent is hereby corrected as shown below:

Column 11, line 14, "and" should read -- the --.

Column 12, line 18, "claim 1" should read -- claim 3 --.

Column 12, line 24, "claim 1" should read -- claim 3 --.

Column 12, line 29, "H" should read -- H. --.

Column 12, line 30, "claim 1" should read -- claim 3 --.

Signed and Sealed this

Twenty-third Day of October, 1990

Attest:

HARRY F. MANBECK, JR.

*Attesting Officer*   *Commissioner of Patents and Trademarks*